United States Patent [19]
Nakazawa et al.

[11] Patent Number: 4,796,643
[45] Date of Patent: Jan. 10, 1989

[54] MEDICAL ELECTRODE LEADS

[75] Inventors: Akira Nakazawa, Balmain; Zoran Milijasevic, Sydney, both of Australia

[73] Assignee: Telectronics N.V., Curacao, Australia

[21] Appl. No.: 913,512

[22] Filed: Sep. 30, 1986

[51] Int. Cl.⁴ ............................................. A61N 1/05
[52] U.S. Cl. ................................. 128/785; 128/786; 128/419 P; 128/642
[58] Field of Search .................. 128/419 P, 784–786, 128/642

[56] References Cited

U.S. PATENT DOCUMENTS

| | | | |
|---|---|---|---|
| 4,198,991 | 4/1980 | Harris | 128/784 |
| 4,407,303 | 10/1983 | Akerstrom | 128/785 |
| 4,519,404 | 5/1985 | Fleischhacker | 128/785 |
| 4,641,664 | 2/1987 | Botvidsson | 128/785 |
| 4,662,382 | 5/1987 | Sluetz et al. | 128/419 P |

FOREIGN PATENT DOCUMENTS 2558376 7/1985 France ........................ 128/785

Primary Examiner—Ruth S. Smith
Attorney, Agent, or Firm—Gottlieb, Rackman & Reisman

[57] ABSTRACT

An electrode lead for a pacemaker which has improved introducing, removal and anchoring characteristics. An insulating covering has at least two rows of loops which fall within a truncated cone with its minimum diameter at the tip.

12 Claims, 4 Drawing Sheets

MEDICAL ELECTRODE LEADS

BACKGROUND OF THE INVENTION

The present invention relates to a medical electrode lead employing a tip configuration to hold the distal tip of the electrode in place. The lead is particularly adapted for use with heart pacemakers.

Today there are currently available many forms of electrode leads which are provided with a metallic distal tip which is placed adjacent to excitable tissue, such as the inside wall of the heart. Electric current is supplied to the distal tip through an interconnected insulated electrode wire to stimulate the heart muscle which is in contact with the tip.

One of the main requirements of a pacing electrode is that the electrode tip be maintained in a stable contact with the heart wall for the entire duration of the implant in a patient. This is particularly difficult during the initial acute stage of about 3 or 4 weeks of implantation while fibrotic material is forming about the lead tip. When such contact is not maintained, either acute or chronic (longer term) there is a potential hazard of pacing system failure due to lead dislodgement from one area of the heart to another where it cannot effectively provide for the stimulating and sensing requirements of the pacing system. Lead dislodgement has been known for some time to be one of the most frequent reasons for lead failure. This is particularly true in the hands of less experienced surgeons. In order to stabilize the position of the lead at the heart wall, a number of surgical and mechanical schemes and also various fixating means have been developed over the years to combat and attempt to overcome this problem. One scheme calls for sustaining the lead within the vein and then immobilizing the patient's arm and shoulder to prevent lead movement while fibrosis occurs.

There have been two types of lead tip mechanical fixating means: the first is sometimes called a passive fixating means and the second an active means. The active means is of the screw-in type wherein a physician manually screws or engages a conductive electrode element into the heart wall. The so-called passive means requires no action of the physician beyond insertion of the lead in the normal manner together with placement of the electrode tip in the apex of the ventricle in the conventional manner. In order to stabilize the position of the lead at the heart wall, such things as wedges and/or tines made of thin, very flexible wire, or elastomeric materials, have been used. Such wire, or elastomeric tines and wedges have been intended to entrap or hold the distal end of the lead in the trabeculae of the heart while the fibrotic material forms around it to hold the lead tip in place.

There are a number of geometrical design requirements placed on the passive lead fixating means so that the lead can (a) pass with minimum resistance through even small veins or lead introducers which are used to introduce leads into a vein, (b) be fixated reliably within the trabeculae, (c) minimize the probability of lead entanglement with other cardiac anatomical structures such as heart valves, and (d) have appropriate mechanical characteristics that enable the lead to be removed after acute or even chronic fixation with a minimum of force. The latter requirement is of particular importance in cases where infection develops at the stimulating site, or when the pacing output of the pacemaker no longer meets the requirements and the lead needs to be repositioned or altered. This often occurs when too much fibrotic material builds up and the stimulation threshold undesirably increases. To withdraw a lead after prolonged chronic implant, substantial forces may be required because of complete fibrotic tissue encapsulation of the tip as well as the tines. There is a possibility of tines tearing off and being left in the body.

An example of a prior art device employing truncated cone sections behind the tip (a so-called wedge tip) is disclosed in Thalen's U.S. Pat. No. 4,030,508. An example of thin, flexible wire tines is shown in Chardack's paper entitled "New Pacemaker Electrodes" published in Vol. XVII of the *Transactions of the American Society of Artificial Internal Organs*, 1971. Another approach employing flexible tines which are located immediately adjacent the electrode tip is shown in U.S. Pat. No. 4,033,357 to Helland. The advent of porous electrodes, which encourage tissue ingrowth, has been an alternative to the tined electrodes as a means for ensuring fibrotic incorporation into the tip to best ensure correct placement against the heart wall. Such porous electrodes have been of the type having a plurality of small holes drilled through the tip as, for example, with the laser, various sponge-metal type tips, or tips comprised of sintered platinum balls, the interstices between which encourage intergrowth with fibrotic material. Some manufacturers have combined porous tips with tines. Another early electrode of the tined elastomer type was the type MIP 135 of *Vitatron Medical N.V.* of Holland. This electrode consisted of a platinum-iridium electrode tip and a helicallycoiled lead of elgiloy insulated by a tube of silicone rubber. The tip was fitted with a small barbed silicone ring to prevent dislocation in the critical post-operative period. This lead is disclosed, for example, in *Biomedical Engineering*, Vol. 4, No. 8, Aug. 1959, page 383. Another tined lead proposal is found in the patent to Citron et al No. 3,902,501, dated Sept. 2, 1975. It is believed the Citron et al lead had no commercial counterpart because of the inability to make the embodiment shown in the patent correctly function. A variety of reasons for this difficulty exist but most of them relate to dimensions of parts. For example, the tines had to be cut for use. The sleeve which was arranged to restrain the tines during implantation did not allow orderly release in the heart. The tines were too long and thus tended to be floppy and difficult to put in place.

In another approach, Doring, in U.S. Pat. No. 4,301,815, described a trailing tined electrode wherein tine-like members extended behind the electrode tip shank so that they could be folded within a cylindrical area smaller than the circumference of the lead tip shank during placement. This significantly reduced the trauma associated with implantation of other types of tine leads, for example, of the Helland or Citron et al type. Another improvement by Doring is shown in U.S. Pat. No. 4,409,994 which consisted of including a recessed portion behind the tip shank where tines could be folded into an area determined by a lap joint thus further reducing the introducer size of the trailing tine lead.

All of the above tines have some difficulty associated with removal after the tine members have been encapsulated in fibrotic material. Another particularly distressing difficulty with the tined lead, especially when used as a trial lead is the propensity for the tip to pass through the tricuspid valve with the tines catching in the chordae tendonae—the thin string-like muscles about the valve. The chordae tendonae get caught in the acute angle joint when the tines meet the tip body and the lead cannot be removed. This type of difficulty does not arise with the wedge tip electrode.

It is an object of the present invention to provide an improvement over electrodes of the wedge type with improved insertion, withdrawal, and acute manipulation characteristics. The molded members of this lead have increased facility for folding back when removal from an entrapped position within the trabeculae is desired. It is another object of the invention to provide an improved lead over the wedge type with increased strength in the molded members. Additionally, if a portion is accidentally torn off, molded members are less likely to be lost in the blood stream.

When we discuss entrapment within the trabeculae upon first placing one of the leads in the heart, we wish to convey the concept of an almost loose, but not quite nonrigid interface of the electrode tip molded parts and the trabeculae. In this relationship, the physician is able to sense the entrapment by gentle tugging on the lead.

SUMMARY OF THE INVENTION

To achieve the foregoing objects, and in accordance with the purposes of the invention, as embodied and broadly described herein, the electrode lead of the present invention comprises an exposed conductive distal tip and a conductive shank supporting the distal tip; an electrical conductor coupled to the proximal end of the shank; an insulating covering over the shank and conductor; and a molded tip connected to the insulating covering at the section where the insulating covering is placed over the conductive shank and the electrical conductive coil for anchoring the electrode lead.

The molded tip of the wedge type consists of molded members. The molded members consist of a plurality but at least two rows of loops having substantially parallel upper and lower surfaces and the outer ends of which fall within the surface of revolution which defines a cone. Normally the distal end is about 2 mm in diameter and the proximal end is about 6 mm in diameter. The upper and lower surfaces or curves of the rows of loops fall in planes which are substantially perpendicular to the longitudinal axis of the lead. The rows are spaced apart a sufficient distance to allow trabeculae to be temporarily entrapped or sectionally engaged perpendicular to the longitudinal axis of the lead. The loops are sufficiently rigid to hold the trabeculae in place yet sufficiently flexible to fold back against the lead body when being passed through a lead introducer and to do so without tearing.

The loops in each common row are of substantially the same horizontal dimensions, that is, they all have approximately the same radius and that radius being substantially perpendicular to the longitudinal axis of the lead. The loops of the smallest and the most distal rows may be generally arcuate tabs rather than apertured loops.

The loops of each successive row are offset from the loops in adjacent rows to allow the temporary entrapment of and preferably frictional engagement with trabeculae.

While in the preferred embodiment there are two rows of loops, in an alternative embodiment there are three with the middle row of loops being bound within a surface of revolution having a diameter of about 4 mm.

After fibrosis occurs, should tugging in an attempt to remove the tip cause one of the loops to tear off, the fibrotic material which has grown through the loop will tend to maintain it in place rather than allowing it to float free as may occur with the small barbs which constitute prior art tines. In another embodiment the tip end and associated molded parts are of conducting material. The conducting material may be formed of particulate carbon, substantially evenly distributed through a silastic carrier in a quantity sufficient to allow the passage of electricity from the metal tip to adjacent tissue. In yet another embodiment there are carbon fibers reinforcing the loops and wedge tip molded member to prevent accidental tearing. The use of reinforcing carbon fibers allows the loops to be made still thinner which facilitates introduction of the lead through an introducer.

It is important to remember that tines are a short-term acute fixation device. Fibrous intergrowth is the long-term means for fixation. The use of a wedge, prior art tines, or the improved construction of this invention are all intended to be short-term acute fixation devices intended to hold a tip in place with the least possible complications to the patients. Short-term acute fixation means should allow for manipulation of the tip should early dislodgement occur, which manipulation should be easily accomplished without injury to the patient. Prior tines tended to be too barbed and could wedge in trabeculae too firmly to allow manipulation. With the wedge tip, manipulation was much easier since there are no sharp edges and joints within which trabeculae or cordae tendonae can catch and substantially permanently wedge/seat. With the improved tip of this invention with the rows of parallel loops there is likewise the ability for easy manipulation without wedging of the trabeculae in removable relationship with the tip. In one embodiment the loops are formed of absorbable ligature material which is absorbed by the body after the acute stage of lead placement.

In one embodiment the apertures through adjacent rows of loops are colinear. This is desirable to prevent accidental wedging of trabeculae between adjacent rows of loops. However, if the rows of loops are sufficiently spaced apart, the wedging is minimized or avoided and an entirely satisfactory improved wedge type tip results.

Another desirable aspect of the parallel rows of loops in the tip lead of this invention is that the loops can be quite thin while maintaining sufficient strength because of the increased surface area of interconnection with the main body of the lead at each end of a given loop. A prior proposed lead has short bars or arms substantially perpendicular to the horizontal axis of the lead to overcome the ability of the tined-type leads to firmly catch trabeculae in the acute angle between the tines and the shank body. However, the loop construction of this invention allows substantially thinner molded elements to be utilized. Of course, with the carbon filament reinforcement above mentioned, even further strength is obtained.

It has been suggested that tines of, for example, the type found in some of the patents above mentioned are not as sharp as metal and thus cause little opportunity for injury to a patient. Even though the tines are made of silicone or polyurethane, they are still sharp and in fact somewhat stiff and tend to be abrasive to sensitive tissue. The use of rounded loops in substantially parallel planes within the surface of revolution of a cone as above described has no sharp edges with which to abrade sensitive internal heart tissue.

DESCRIPTION OF THE DRAWINGS

A greater appreciation of the objects and advantages of the invention may be understood by a detailed description taken in conjunction with the drawings wherein.

DETAILED DESCRIPTION

Figure 1:
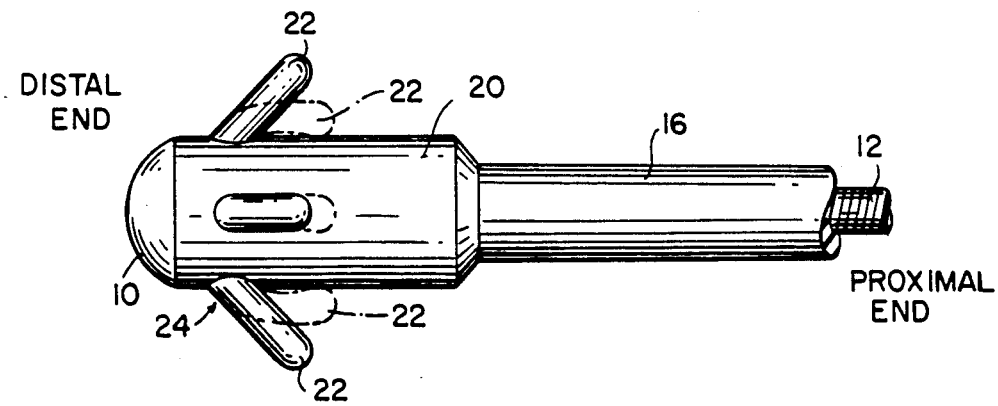
FIG. 1 illustrates a prior art electrode lead of the type having tines adjacent to an electrode tip.

Referring to FIG. 1, there is shown a prior art tined electrode lead having an exposed distal tip 10 and an electrical conductor 12 for electrically connecting a pulse of current from a pacemaker, not shown, at the proximal end of conductor 12 to the distal tip 10. For the purposes of the description, and as used herein, "distal" refers to that end of the electrode lead or any part of the electrode lead nearest to the muscle to be stimulated and "proximal" refers to that end of the electrode lead or any part of the electrode lead nearest to the source of the pulses, such as a pacemaker. Distal tip 10 may contain a center insulating section, but must at least in part be conductive.

Electrical conductor 12 is typically a helically wound wire or plurality of interwound wires which is known in the art as a "helix" or a coil and which exhibits flexibility and strength. Distal tip 10 is typically supported by a conducting shank (not shown) encapsulated within the insulating coating 20.

The insulating coating 16 is of smaller diameter but interconnected with the section 20. There is a plurality of tines 22 fixed to the section 20 adjacent the tip 10. The tines are flexible but relatively thick. In an unrestrained configuration, the tips form an acute angle with the axis of the shank or conductor 12. The coating 16 and 20 comprises silicone rubber or other flexible nonconductive material which is inert to body fluids. Certain types of polyurethane are also used.

During insertion, the tines 22 are bent back adjacent the section 20 as generally shown in dotted lines in FIG. 1. It should be noted that since the tines 22 are attached to the outer surface of section 20 adjacent the tip, there is an abrupt transition zone at 24 to any obstacle encountered upon insertion of the electrode lead, i.e. a narrowing in the vein, a small bore introduction catheter, and the like. It should also be noted that when folded the tines present a minimum cross-sectional width considerably larger than the width of the section 20 of the lead. This abrupt transition zone and the magnitude of the cross-sectional width limit the utility of such electrodes in small openings such as small veins found in children. The transition zone tends to be traumatic in insertion. The acute angle between the tines 22 and section 20 often becomes wedged into contact with chordae tendonae and trabeculae making further acute head manipulation impossible.

Figure 2:
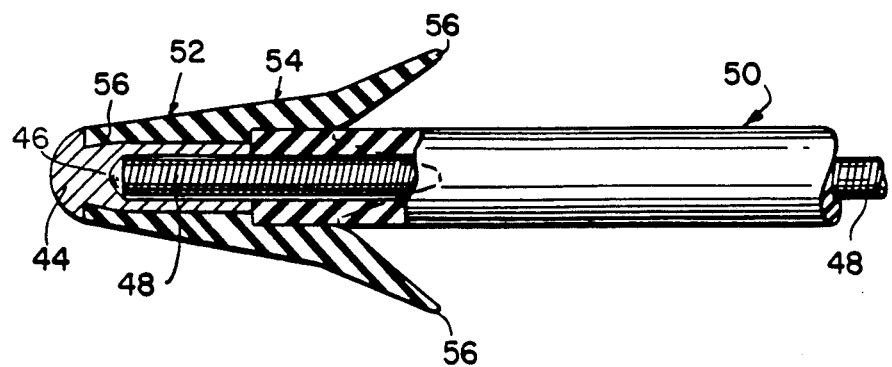
FIG. 2 is illustrative of a prior art electrode of the trailing tine type showing tines placed behind the electrode tip to reduce folded diameter.

As shown in FIG. 2, which is a partially cut-away side elevation of another type of tined lead called the trailing tine, distal tip 44, is interconnected through shank 46 to a coiled conductor 48. Insulating coating 50 covers the conductor 48, and includes the first section 52, the second section 54, and tines 56. All is described in more detail in Doring Pat. No. 4,301,815 above referred to.

The present invention provides further improvements on the lead designs illustrated in FIGS. 1 and 2 and is intended to provide a better facility for the lead tip to be held in place during the acute phase of lead insertion, yet facilitate physician manipulation in the same phase and further facilitate lead removal when that is necessary, or useful.

Figure 3B:
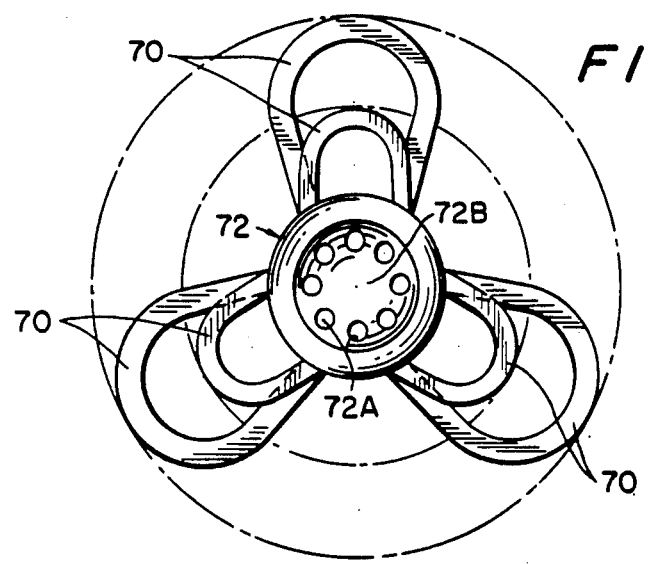
FIG. 3B is a top view of the lead of FIG. 3A.
Figure 3A:
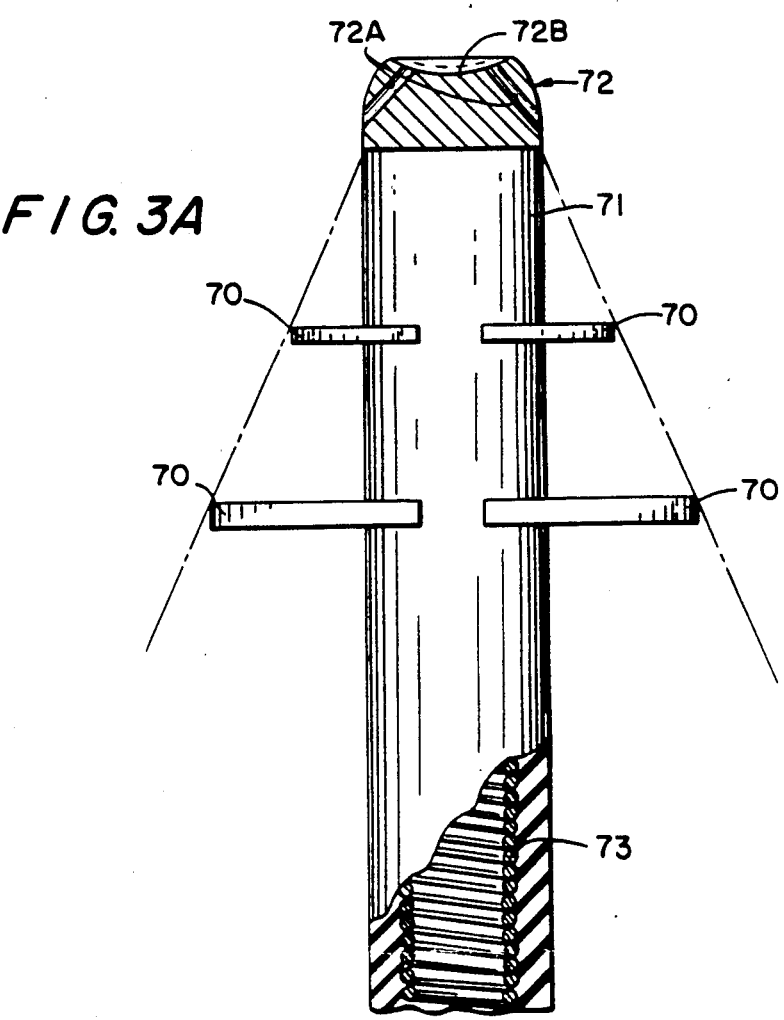
FIG. 3A is a side elevation in partial section of a preferred embodiment of an electrode according to the present invention.

In FIGS. 3a and 3b there is shown a lead according to this invention consisting of a helically wound conductive coil 73 which at its distal end terminates in a conductor tip 72. The tip is of the apertured dish type in a preferred embodiment with a plurality of apertures 72A formed through the arcuately indented dish tip face 72B. A tine molding 71 is mounted about the conductor tip 72 and the distal tip of the helically-wound coil 73. There is a plurality of rows of loops 70 which extend outwardly from the molding at an angle perpendicular to the longitudinal axis of the lead.

Figure 5:
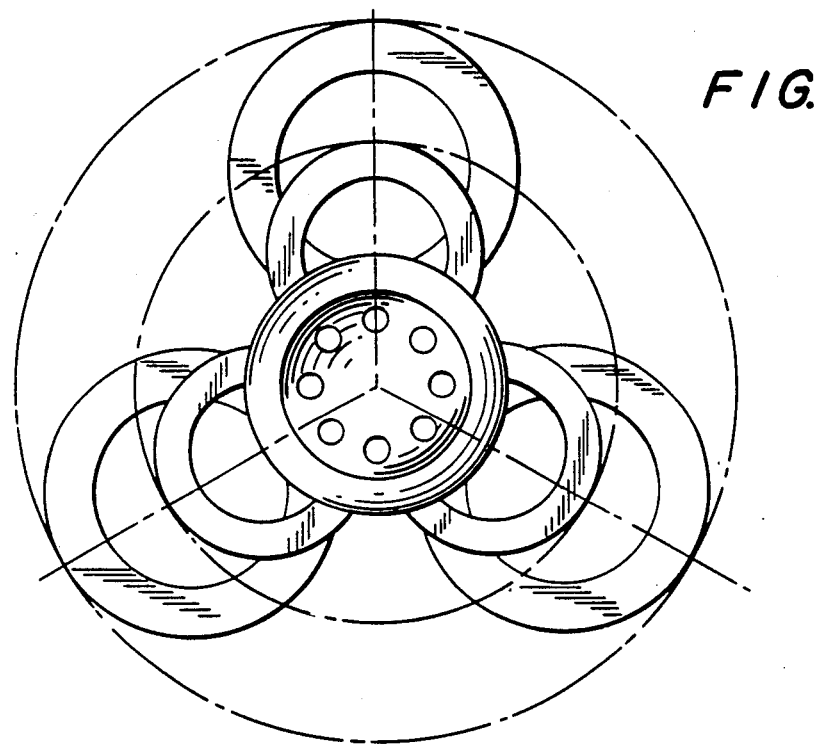
FIG. 5 is an alternative to FIG. 3B employing circular loops.

Referring further to FIGS. 3A and 3B, the diameter of the tip is approximately 2.2 mm. The first row of loops is approximately 3/10 of a millimeter in thickness and the second row is about 5/10 of a millimeter in thickness. The first row of loops is adjacent the metal tip. The bottom row is about 4 mm from the tip front face. In the preferred embodiment the molded portions of the lead are silicone rubber. Polyurethane is also equally satisfactory. With polyurethane the lead and loops can be still smaller in cross-sectional dimensions. The tip 72 with its upwardly opening dished face 72B and apertures 72A is of the type currently sold by Telectronics, Inc. under the name "Laserdish Tip Electrode." All parts of the lead (other than the wedge type molded tip parts herein disclosed) are approximately to scale and are substantially those of the commercially distributed Laserdish Tip Electrode. FIG. 5 is an alternative to FIG. 3B employing circular loops which are easier to manufacture than noncircular loops.

Figure 4B:
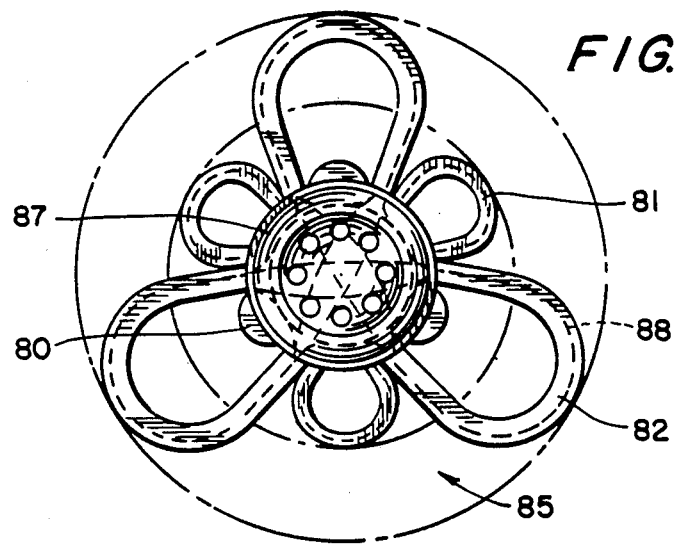
FIGS. 4A and 4B show an alternate preferred lead wherein electrically conductive carbon fibers are used to reinforce the molded portions of the tip, wherein three rows of loops are shown, wherein the molded tip center portion is slightly wider than the body of the lead, and wherein the loops in successive rows are offset from each other.
Figure 4A:
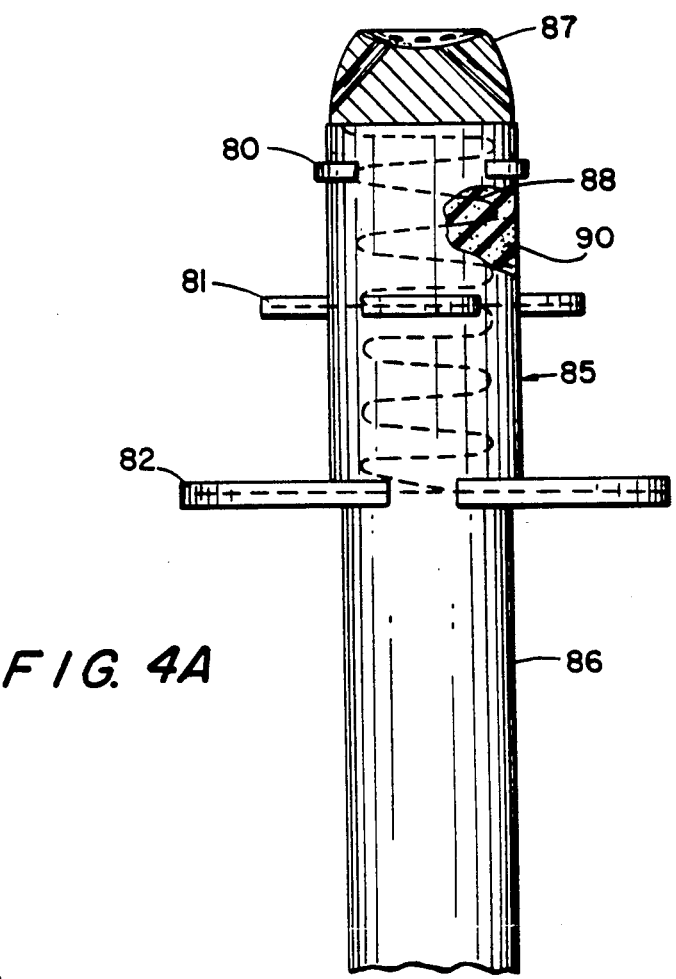
Figure 6:
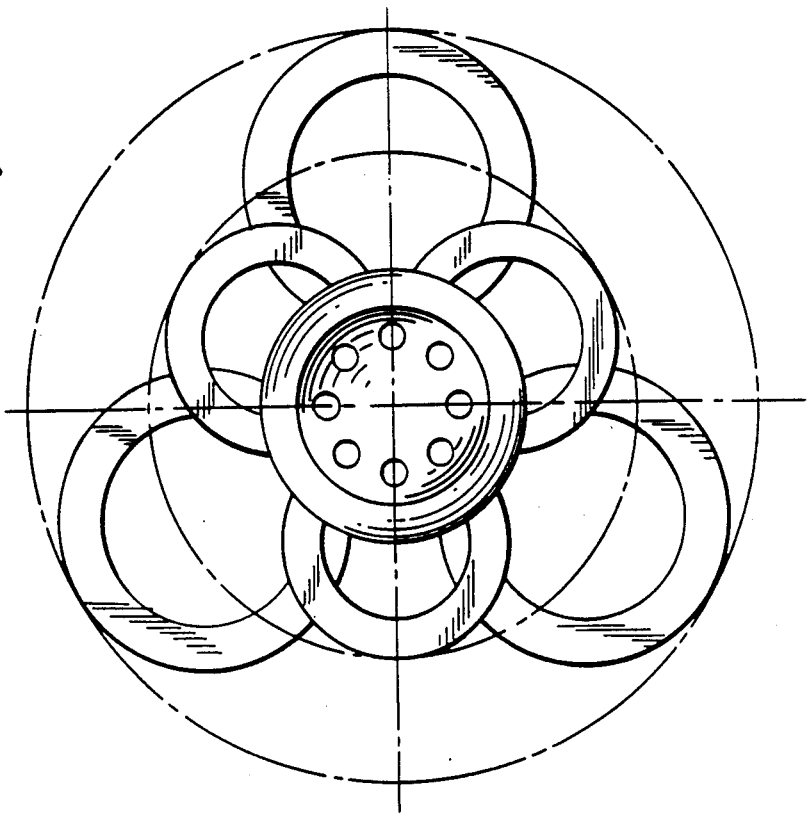
FIG. 6 is an alternative to FIG. 4B employing circular loops.

Referring now to FIGS. 4A and 4B, there is shown three layers or rows of loops, 80, 81 and 82. Note the row of elements 80 are simply tabs. Tabs are useable for the shorter loop members. Preferably, however, each layer is of loop configuration. The portion 85 of the tip molded central member is of slightly larger diameter than the portion 86 to allow the longer loops 82 to easily fold back against the lead body when it is being passed through the introducer. The same dished tip, apertured, body-contacting portion 87 is found at the distal tip of the lead. A plurality of carbon fibers or filaments 88 are shown reinforcing the loops and lead body. They are preferably electrically interconnected with the tip 87. At least acutely it is useful to have the loops and molded tip portion electrically conductive to allow better capture. As the tip and its molded elements are fibrosed, the electrical conduction between the electrically-conductive loops 80, 81 and 82 substantially diminishes to almost zero with current flow being just through the tip 87. In addition, particulate electrically conductive carbonaceous material 90 may be distributed through the molded silastic member. Of course, the carbonaceous material may be used separately from the carbon filaments and vice versa. FIG. 6 is an alternative to FIG. 4B employing circular loops which are easier to manufacture than non-circular loops.

In yet another embodiment of the invention, the loops are made of moldable soluble ligature material or biodegradable polymer in loop form. Such a soluble ligature material is formed from an acrylic compound such as coated Vicryl (tradename) comprising polyglactin 910 suture (a copolymer consisting of 90% glycolic acid and 10% lactic acid) coated with polyglactin 370 (a copolymer consisting of 30% glycolic acid and 70% lactic acid) and calcium stearate. This material will hold the tip in place through the acute stage while fibrosis is occurring and, for example, intergrowth through the apertures in the tip occurs. After the acute stage the body absorbs the ligature loops. This makes removal of the lead more possible in the chronic stage.

Having thus described the invention in detail and with sufficient particularity as to enable one skilled in the art to practice, what is claimed as our invention is set forth in the following claims.

1. An electrode lead for engaging trabeculae having a lead body with an exposed conductive distal tip in a conductive shank supporting the distal tip, said conductive shank having a proximal end, there being an electrical conductor coupled to the proximal end of said shank, insulating means for insulating said shank and the conductor, said insulating means including molded anchoring means, said molded anchoring means comprising at least two rows of loop means having substantially parallel upper and lower surfaces within substantially parallel planes substantially perpendicular to the longitudinal axis of the lead body, the rows of loop means being spaced apart for independent motion a sufficient distance to allow trabeculae to be temporarily entrapped perpendicular to the longitudinal axis of the lead body, said loop means being sufficiently rigid to hold the trabeculae frictionally in place yet sufficiently flexible to be adapted to fold back against the lead body when being passed through a lead introducer and into the heart without tearing the loop means.

2. An electrode according to claim 1 wherein the loop means in each row are of substantially the same horizontal dimensions as other loop means in the row.

3. An electrode according to claim 2 wherein the loop means of the first row are tabs.

4. An electrode according to claim 1 wherein the loop means of the first row are tabs.

5. An electrode according to claim 1 wherein the loop means of each successive row is offset from the loop means of the adjacent row.

6. An electrode according to claim 5 wherein the loop means of the first row are tabs.

7. An electrode according to claim 1 wherein the loop means in each row have apertures which are substantially co-linear.

8. An electrode according to claims 5 or 7 wherein the loop means in each row are of substantially the same horizontal dimensions as other loop means in the row.

9. An electrode according to claim 1 wherein said loop means falls within and has tips substantially coincident with a surface of revolution of a truncated cone which is about 2 mm in diameter and about 6 mm in diameter at the base.

10. An electrode according to claim 1 wherein conducting carbonaceous material is substantially uniformly distributed through the molded means.

11. An electrode according to claim 10 wherein said carbonaceous material comprises reinforcing carbon fibers electrically conductively interconnected with the tip.

12. An electrode according to claim 1 wherein said loop means is constructed and molded of a soluble material which is absorbed by the body after an acute period of implantation.

* * * * *